US012655480B2

(12) United States Patent (10) Patent No.: US 12,655,480 B2

Lauber et al. (45) Date of Patent: Jun. 16, 2026

(54) SAMPLE PREPARATION FOR LC-MS BASED SEQUENCE MAPPING OF NUCLEIC ACIDS

(71) Applicant: Waters Technologies Corporation, Milford, MA (US)

(72) Inventors: Matthew A Lauber, North Smithfield, RI (US); Xiaoxiao Liu, Natick, MA (US)

(73) Assignee: Waters Technologies Corporation, Milford, MA (US)

( * ) Notice: Subject to any disclaimer, the term of this patent is extended or adjusted under 35 U.S.C. 154(b) by 800 days.

(21) Appl. No.: 17/961,061

(22) Filed: Oct. 6, 2022

(65) Prior Publication Data

US 2023/0111049 A1 Apr. 13, 2023

Related U.S. Application Data

(60) Provisional application No. 63/253,616, filed on Oct. 8, 2021.

(51) Int. Cl.
| | |
|---|---|
| *C12Q 1/68* | (2018.01) |
| *C12Q 1/6872* | (2018.01) |
| *C12Q 1/6806* | (2018.01) |

(52) U.S. Cl.
CPC ......... *C12Q 1/6872* (2013.01); *C12Q 1/6806* (2013.01)

(58) Field of Classification Search
CPC ............................. C12Q 1/6872; C12Q 1/6806
See application file for complete search history.

(56) References Cited

U.S. PATENT DOCUMENTS

2006/0160125 A1 7/2006 Kool

FOREIGN PATENT DOCUMENTS

| | | |
|---|---|---|
| WO | 2006031745 A2 | 3/2006 |
| WO | 2013188846 A1 | 12/2013 |
| WO | 2018081462 A1 | 5/2018 |

OTHER PUBLICATIONS

Hengen. "Methods and reagents." Trends Biochem. Sci. 21.3(1996): 112-113.
Holley et al. "A Simplified Procedure for the Preparation of Tyrosine and Valine-Acceptor Fractions of Yeast "Soluble Ribonucleic Acid"." J. Biol. Chem. 236.1: 200-202. 1961.
Pasloske. "Ribonuclease Inhibitors." Nuclease Methods and Protocols. Totowa, NJ: Humana Press. (2001): 105-111.
Sweeney et al. "A highly active immobilized ribonuclease." Anal. Biochem. 286.2(2000): 312-314.
Gasmelseed et al. "Low Frequency of Deafness-associated GJB2 Variants in Kenya and Sudan and Novel GJB2 Variants." Human Mutation: Mutation in Brief #687. 2004.
Hahner et al. "Matrix-Assisted Laser Desorption/Ionization Mass Spectrometry (MALDI) of endonuclease digests of RNA." Nucl. Acids Res. 25.20(1997): 1957-1964.
International Search Report and Written Opinion issued in International Patent Application No. PCT/IB2022/059571 dated Jan. 20, 2023.
Kyslik et al. "The myxozoan minicollagen gene repertoire was not simplified by the parasitic lifestyle: computational identification of a novel myxozoan minicollagen gene." BMC Genomics. 22.1(2021): 1-14.
Liu et al. "The mechanism of base excision repair in Chlamydiophila pneumoniae." DNA Repair. 4(2005): 1295-1305.

*Primary Examiner* — Jezia Riley
(74) *Attorney, Agent, or Firm* — WOMBLE BOND DICKINSON (US) LLP; Deborah M. Vernon

(57) ABSTRACT

Methods for quenching a nuclease digestion of a target nucleic acid prior to downstream analysis of the target nucleic acid are disclosed herein. Particularly, methods for controlling the end point of a nuclease digestion prior to sequence analysis of a target nucleic acid is provided. Quenching of a nuclease digestion in the present disclosure employs at least one non-ionic or anionic denaturant combined with an optional reducing agent. The methods presented in this disclosure aids preserving the sample comprising the target nucleic acid or fragments thereof for long term storage and ensures that the effect of contaminating nucleases is eliminated during pretreatment step.

14 Claims, 3 Drawing Sheets

SAMPLE PREPARATION FOR LC-MS BASED SEQUENCE MAPPING OF NUCLEIC ACIDS

CROSS-REFERENCE TO RELATED APPLICATION

This application claims priority and benefit to U.S. Provisional Patent Application No. 63/253,616, filed on Oct. 8, 2021, and entitled "SAMPLE PREPARATION FOR LC-MS BASED SEQUENCE MAPPING OF NUCLEIC ACIDS", the contents of which is incorporated herein by reference in its entirety.

FIELD OF THE TECHNOLOGY

The present disclosure relates generally to methods for quenching a nuclease digestion of a nucleic acid prior to downstream analysis. In particular, methods for controlling the end point of a nuclease digestion prior to sequence analysis of a target nucleic acid are provided herein. Quenching of a nuclease digestion in the present disclosure employs at least one non-ionic or anionic denaturant combined with an optional reducing agent. The present disclosure further provides methods for controlling fragment length of a target nucleic acid prior to sequencing analysis, particularly LC-MS analysis. This disclosure also provides methods for reducing/eliminating the effect of contaminating nucleases during a pretreatment step.

BACKGROUND

Characterization of nucleic acid sequences is a critical aspect of RNA/DNA based drug development and regulatory approval. Sequencing of nucleic acid is traditionally performed by either Sanger sequencing or so-called Next Generation Sequencing. However, these approaches are limited in terms of the molecular detail they can elucidate. In combination with these techniques, it is desired to have orthogonal methods for a panoramic view. Robust liquid chromatography (LC) and mass spectrometry (MS) approaches have been used to confirm identity, observe primary sequence and to precisely measure modified residues and important structural motifs of a nucleic acid, such as the 5' endcap and polyA tail of an mRNA molecule.

Yet, sample preparation techniques greatly affect the results obtained from these orthogonal methods. During pretreatment of nucleic acids and their storage, nucleic acids encounter nucleases, both advertently and inadvertently. For example, nucleases are often added with the intent of digesting/fragmenting nucleic acids in a sample prior to an analytical sequential analysis method. However, nucleases are difficult to inhibit and control when they are applied as a sample preparation tool, and this leads to undesired fragmentation, e.g. very short fragments that are not suitable to be analyzed with a chosen analytical method. In addition, human skin is an abundant source of nucleases that can be transferred accidentally to surfaces and solutions (Holley, R. W.; Apgar, J.; Merrill, S. H. J. Biol. Chem. 1961, 236, PC42-43.) Moreover, reagents used during sample preparation are often contaminated with nucleases (Hengen, P. N. Trends Biochem. Sci. 1996, 21, (3), 112-113). Therefore, if not quenched/control properly, whether added advertently or inadvertently, residual amounts of these nucleases can adversely affect downstream steps in protocols. (Pasloske, B. L. In Nuclease Methods and Protocols, Schein, C. H., Ed. Humana Press: Totowa, N.J., 2001, pp.105-111; Sweeney, R.

Y.; Kelemen, B. R. Woycechowsky, K. J.; Raines, R. T. Anal. Biochem. 2000, 286, (2), 312-314).

SUMMARY

In general, it is an object of the present technology to obviate or mitigate at least one disadvantage of previous methods for controlling/inactivating digestion ability of contaminating nucleases and/or an intended nuclease that is added during sample preparation step prior to a downstream analytical method. In some embodiments, the downstream analytical method is LC-MS method, specifically ion pairing reversed phase liquid chromatography (IP-RPLC)-MS method.

In general, sample pretreatment methods of the present technology can be utilized to control the amount of digestion (e.g., an end point of digestion) from an applied nuclease digest. As a result of controlling or quenching digestion, a digested/pretreated sample can be preserved for a significant period of time (e.g., days to weeks) facilitating repeat analyses and sample archiving. Quenching techniques of the present technology are compatible with desired orthogonal downstream analysis such as ion pairing reversed phase liquid chromatography (IP-RPLC).

In one aspect, provided herein is a method for sequence analysis of a target nucleic acid present in a sample comprises the steps of: (a) treating the sample with a nuclease free buffer comprising a first optional denaturant and an optional metal-chelation agent to denature the target nucleic acid; (b) incubating the sample with a nuclease enzyme for a predetermined amount of time, wherein the nuclease is capable of fragmenting the target nucleic acid to produce a set of nucleic acid fragments each containing a sequence that corresponds to a sequence of the target nucleic acid; (c) inactivating the fragmenting capability of the nuclease enzyme by addition of a second denaturant and an optional disulfide bond reducing agent; (d) subjecting the set of nucleic acid fragments to a single-mode or a multiple mode of chromatography followed by a mass spectrometry (MS) method; and (e) generating mass signals of the set of nucleic acid fragments by the mass spectrometry method whereby determining the sequence of the target nucleic acid from the mass signals.

In some embodiments, the first optional denaturant and the second denaturant is independently selected from the group consisting of non-ionic and anionic denaturants.

In some embodiments, the first optional denaturant and the second denaturant is selected from same chemical reagent.

In some embodiments, the first optional denaturant is absent.

In some embodiments, the target nucleic acid is selected from the group consisting of a single stranded DNA, a double stranded DNA, cDNA, a single stranded RNA, a double stranded RNA, a DNA/RNA hybrid, and a DNA/RNA mosaic nucleic acid.

In some embodiments, the optional disulfide bond reducing agent is selected from the group consisting of dithiothreitol (DTT), ethylenediaminetetraacetic acid (EDTA), 2-mercaptoethanol, 2-mercaptoethylamine-HCl, (Tris(2-Carboxyethyl)phosphine)(TCEP), N-ethylmaleimide, cystein, or glutathione.

In some embodiments, the nuclease enzyme is selected from the group consisting of endonucleases and exonucleases. The endonucleases are selected from the group consisting of restriction enzymes, RNA endonucleases, DNA endonucleases and non-specific phosphodiesterases.

In specific embodiments, the RNA endonucleases are selective or non-selective RNA endonucleases and the target nucleic acids is a single stranded RNA or a double stranded RNA. Specifically, the RNA endonucleases are selected from the group consisting of RNase T1, RNase H, Cusativin, MazF, or Colicin E.

In some embodiments, the first optional denaturant and the second denaturant is independently selected from the group consisting of ureas, thioureas, sulfonylureas, semicarbazides, hydrazides, thiosemicarbazides, chaotropes, or salts thereof. Specifically, the first optional denaturant and the second denaturant is independently selected from a group consisting of sodium thiocyanate, potassium thiocyanate, sodium dodecyl sulfate (SDS), urea, sodium iodide, sodium perchlorate, urea, a detergent, or salts thereof. In one embodiment, the first optional denaturant and the second denaturant comprises urea, or a salt thereof.

In some embodiments, the length of the target nucleic acid is about 101 to about 105 individual nucleotides. In some embodiments, the length of the target nucleic acid is about 101 to about 104 individual nucleotides. In some embodiments, the length of the target nucleic acid is about 5 to about 100,000 individual nucleotides. In some embodiments, the length of the target nucleic acid is about 15 to about 10,000 individual nucleotides. In some embodiments, the length of the target nucleic acid is about 5 to about 2500 individual nucleotides. In some embodiments, the length of the target nucleic acid is about 101 to about 103 individual nucleotides. In some embodiments, the length of the target nucleic acid is about 10 to about 5000 individual nucleotides. In some embodiments, the length of the target nucleic acid is about 30 to about 2000 individual nucleotides. In certain embodiments, the length of the target nucleic acid is about 50 to about 1500 individual nucleotides. In certain embodiments, the length of the target nucleic acid is about 100 to about 1000 individual nucleotides.

In some embodiments, subjecting the set of nucleic acid fragments to a single-mode or a multiple mode of chromatography is further followed by one or more ionization and/or sampling technique known in the art to hyphenate the single-mode or the multiple mode of chromatography to the mass spectrometry (MS) method.

In some embodiments, the single-mode or the multiple mode of chromatography followed by a mass spectrometry (MS) method comprises a reverse phase separation, a cation exchange separation, an anion exchange separation, an ion pair separation, normal phase separation, an ion mobility separation, a size-exclusion separation, a chiral separation, an affinity separation, a ligand exchange separation, a polar nonionic separation, or any combination thereof. In certain embodiments, the single-mode or the multiple mode of chromatography is ion pairing reversed phase liquid chromatography (IP-RPLC). In some embodiments, the single-mode or the multiple mode of chromatography is coupled with an UV detection system.

In some embodiments, the mass spectrometry method is selected from the group consisting of Matrix-Assisted Laser Desorption/Ionization-Time-of-flight (MALDI-TOF), Electrospray-Ionization (ESI), charge detection mass spectroscopy, and Fourier Transform-Ion Cyclotron Resonance (FT-ICR). In some embodiments, the mass spectrometry method is coupled with an UV detection system.

In some embodiments, concentration of the second denaturant is between about 1M and about 10 M, between about 2 M to about 8 M, or between about 4 M to 8 M. In certain embodiments, concentration of the second denaturant is about 6 M.

In some embodiments, concentration of the second denaturant is greater than concentration of the first optional denaturant. In some embodiments, concentration of the second denaturant is at least 10 times greater than concentration of the first optional denaturant. In some embodiments, concentration of the second denaturant is at least 100 times greater than concentration of the first optional denaturant. In some embodiments, the concentration of the second denaturant is at or above its saturation level (e.g., 1M to about 10 M, between about 2 M to about 8 M, or between about 4 M to 8 M).

In another aspect provided herein is a method of pretreating a target nucleic acid present in a sample prior to performing an analytical method comprises the steps of: (a) incubating the sample with a nuclease enzyme for a predetermined amount of time, wherein the nuclease is capable of fragmenting the target nucleic acid to produce a set of nucleic acid fragments each containing a sequence that corresponds to a sequence of the target nucleic acid; (b) inactivating or controlling the fragmenting capability of the nuclease enzyme by addition of a denaturant and an optional disulfide bond reducing agent; and preserving the sample for a certain period of time prior to performing the analytical method. In certain embodiments, the denaturant is urea, or salts thereof.

In some embodiments, incubating sample may occur on ice or at any temperature between −30° C. and 70° C. A sample may be incubated at 25° C.

In some embodiments, pretreating a target nucleic acid present in a sample is a part of sample preparation method prior to an analytical method for sequence analysis of the target nucleic acid.

In some embodiments, step (a) and step (b) are performed simultaneously, thereby the predetermined time is zero.

In some embodiments, the predetermined time is between 0.5 seconds to 60.0 minutes.

In some embodiments, the certain period of time is between 5 minutes to 6 months. In some embodiments, the certain period of time is between 5 minutes to 3 months. In some embodiments, the certain period of time is between 5 minutes to 6 weeks. In some embodiments, the certain period of time is three days. In some embodiments, the certain period of time is one week.

In some embodiments, preserving the sample for a certain period of time comprises preserving the sample in a refrigerator at 4° C. to 8° C. In some embodiments, preserving the sample for a certain period of time comprises preserving the sample in a freezer at −10° C. to −90° C.

In some embodiments, the step (c) inactivating the fragmenting capability of the nuclease enzyme further comprises a heating step before or after the addition of the denaturant and an optional disulfide bond reducing agent. The heating step comprises maintaining temperature between 30° C. to 80° C. for at least 30 seconds or more. In some embodiments, concentration of the denaturant is between about 2M and about 8M. In some embodiments, the denaturant is 6 M urea, or salts thereof.

In some embodiments, the method of pretreating a target nucleic acid present in a sample prior to performing an analytical method further comprises treating the sample with a nuclease free buffer comprising a first denaturant and a metal-chelation agent prior to step (a). In some embodiments, the first denaturant is selected from the group consisting of ureas, thioureas, sulfonylureas, semicarbazides, hydrazides, thiosemicarbazides, chaotropes, or salts thereof. In some embodiments, the first denaturant is independently selected from the group consisting of anionic denaturants.

In one aspect provided herein is a method of preserving a sample prior to LC-MS method, wherein the sample comprises a set of nucleic acid fragments each containing a sequence that corresponds to a sequence of a target nucleic acid and a nuclease enzyme, comprises the steps of; (a) adding a denaturant and an optional disulfide bond reducing agent to the sample; and (b) preserving the sample for a certain period of time prior to the LC-MS method. In some embodiments, the denaturant is urea or a salt thereof.

In some embodiments, concentration of the denaturant is between about 2M and about 8M. In some embodiments, the denaturant is selected from a group of non-ionic or anionic denaturant. Specifically, in some cases, the denaturant is urea, or a salt thereof.

In some embodiments, LC-MS method is reversed-phase ion pairing liquid chromatography (RPIP-LC)-MS method.

In another aspect, provided herein is a method of controlling fragment length of a target nucleic acid prior to downstream sequencing analysis, comprising the steps of: (a) incubating the sample with a nuclease enzyme for a predetermined amount of time, wherein the nuclease is capable of fragmenting the target nucleic acid to produce a set of nucleic acid fragments each containing a sequence that corresponds to a sequence of the target nucleic acid; and (b) quenching the fragmenting capability of the nuclease enzyme by addition of a denaturant comprising urea or a salt thereof and an optional disulfide bond reducing agent, thereby controlling the fragment length of the target nucleic acid, wherein the fragment length depends on the predetermined amount of time.

In some embodiments, the predetermined amount of time is less than 1 second. In some embodiments, incubating and quenching occurs substantially simultaneously.

In another aspect, provided herein is a method of controlling fragment length of a target nucleic acid prior to downstream sequencing analysis, comprising the steps of: (a) incubating the sample with a nuclease enzyme for a predetermined amount of time, wherein the nuclease is capable of fragmenting the target nucleic acid to produce a set of nucleic acid fragments each containing a sequence that corresponds to a sequence of the target nucleic acid; and (b) quenching the fragmenting capability of the nuclease enzyme by addition of a denaturant comprising urea or a salt thereof and an optional disulfide bond reducing agent, thereby resulting in more than 10%, 20%, 30%, 40%, preferably 50% missed cleavage rate within the target nucleic acid sequence.

In another aspect, provided herein is a method for sequence analysis of an intact nucleic acid present in a sample comprises the steps of: (a) incubating the sample with a non-ionic or ionic denaturant and an optional disulfide bond reducing agent, wherein the concentration of the denaturant is at or above its saturation level e.g., 1M to about 10 M, between about 2 M to about 8 M, or between about 4 M to 8 M; (b) subjecting the intact nucleic acid to a single-mode or a multiple mode of chromatography followed by a mass spectrometry (MS) method; and (e) generating mass signals of the intact nucleic acid by the mass spectrometry method whereby determining the sequence of the intact nucleic acid from the mass signals.

The methods disclosed herein advantageously provide ways to quench incomplete digestion of a nuclease during a pretreatment step of a target nucleic acid or a sample comprising a sample nucleic acid. The method for quenching incomplete digestion of a nuclease is also useful for controlling fragment length of a target nucleic acid.

The methods provided in this disclosure is also advantageous for inactivating contaminating nucleases secreted from cells and tissues, skin, airborne bacteria and/or fungi.

The present disclosure provides many advantages including controlling the end point of a nuclease digest and preserving the state of the sample for long lengths time that would facilitate repeat analyses and sample archiving. The methods presented in the present disclosure effectively halts the nuclease used during the digestion step from further hydrolyzing the target nucleic acid. It also helps preserve the sample for long term storage and ensures that contaminating nucleases will also be inactivated during pretreatment step.

In addition, the composition used in the present methods e.g. non-ionic denaturant or ionic denaturant and an optional disulfide reducing agent are compatible with most of the downstream analytical method, e.g., an IP-RPLC separation.

BRIEF DESCRIPTION OF THE DRAWINGS

The technology will be more fully understood from the following detailed description taken in conjunction with the accompanying drawings, in which:

FIG. 2A shows analysis of the sample on an ACQUITY H-Class Bio Binary and Vion IMS QT of within 12 hours of sample preparation. FIG. 2B shows analysis on an ACQUITY I-Class Binary FTN after 3 days of storage at 8° C.

DETAILED DESCRIPTION

Figures 1A, 1B, 1C:
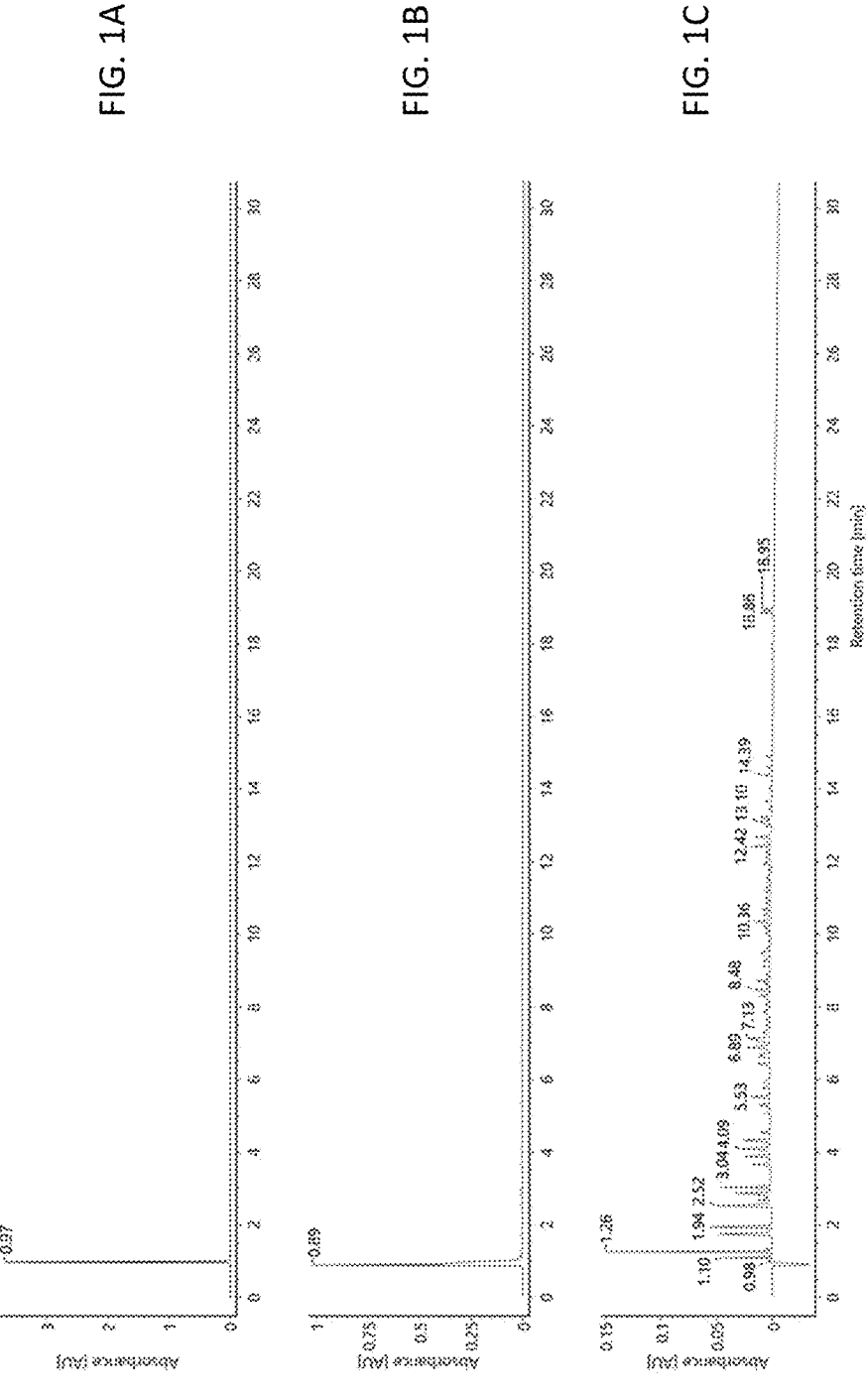
FIG. 1A, FIG. 1B and FIG. 1C provide chromatograms for the separation of Luciferase mRNA which is pretreated in three different ways. The results shown in FIG. 1A are of a 5 min RNase T1 digest that is quenched with DMSO. The chromatogram shown in FIG. 1B shows the results of a pretreatment using guanidinium hydrochloride. And the results shown in FIG. 1C illustrate a pretreatment method of the present technology, using urea. The impact of different quenching methods on IP-RPLC can be seen by comparing FIG. 1A, FIG. 1B and FIG. 1C.

Nucleases are not only ubiquitous in all environments, including the laboratory, but also they are difficult to inhibit and control when they are applied as a sample preparation tool prior to an analytical method, e.g. LC-MS sequence analysis method. It is believed that no technique exists for controlling the end point of a nuclease digest and preserving the state of the sample for long lengths time, e.g., up to 6 weeks that would facilitate repeat analyses and sample archiving. Most especially, no quenching technique has been established that can directly facilitate LC-MS analyses, for example ion pairing reversed phase liquid chromatography (IP-RPLC) analyses.

The sequence mapping of mRNA by LC-MS can be viewed as being highly similar to peptide mapping of proteins. In a peptide mapping sample preparation, it is widely practiced to quench a proteolytic digestion by changing the pH of the digestion mixture. Tryptic digestions are commonly quenched through the addition of an acid, such as trifluoroacetic acid or formic acid. This serves to provide more reproducible end points for the sample preparation and to minimize over digestion. Ideally, a similar practice would be applied to nuclease digestions of nucleic acid. However, the technique for achieving an effective quenched condition has not been devised nor consider in terms of its compatibility to the preferred LC separation mode, an IP-RPLC separation. A pH change to the digestion mixture is not advised because nucleic acids are susceptible to degradation at low and high pH values, if not in the form of hydrolysis on the phosphate backbone then in the form hydrolytic depurination. Alternative quenching procedures are needed as the methods applied to protein sample preparation is not applicable.

In one aspect, quenching a nuclease digestion and preserving a sample for repeat analysis or archiving as well as producing it in a ready to analyze sample composition is provided herein. In one aspect, methods disclosed herein employ use of high concentrations e.g., higher than 2 M of a non-ionic or anionic denaturant combined with the optional addition of a reducing agent.

The methods presented herein temporarily or permanently halt the nuclease activity used in the pretreatment step which is a part of a sample preparation process prior to an analytical method. The methods presented herein can also control the fragmentation of a target nucleic acid, e.g., fragment lengths and/or cleavage points. Nucleases have ability to digest nucleic acids into fragments each containing a sequence that corresponds to a sequence of the target nucleic acid.

The term "inhibit" as applied herein to the activity of nucleases means that the activity of at least one nuclease, e.g. at least one RNase or at least one DNase, is reduced in a sample to which a method of this disclosure is applied, compared to the activity in an analogous sample to which the method of this disclosure is not applied. Inhibition is not limited to complete inhibition or inactivation of a given nuclease. In a given application, it may be that some low level of nuclease activity can be tolerated that will not have a detrimental effect on the outcome of the downstream analysis being performed.

As used herein, the term "denaturant" refers to any compound or material that causes partial or complete nonfolding of a polymer, e.g., a nucleic acid, or a protein.

As used herein, the terms "nuclease inactivation" or the "inactivation of nucleases" denotes that there is no detectable degradation of the sample DNA or RNA under the assay conditions used, and that the nuclease is irreversibly rendered inoperative.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "sample" refers to any medium that includes an analyte (e.g. mRNA) to be processed using the methods according to the present disclosure. A sample may be selected from an agricultural sample, an environmental sample, or a biological sample. A biological sample may include, but is not limited to, for example, a clinical specimen (e.g., blood, plasma, serum, sputum, tissue, urine, saliva, sample/fluid from the respiratory tract, etc.), and cosmetic and pharmaceutical products (e.g., lotions, creams, ointments, solutions, medicines, eye and ear drops, etc.).

As used herein, the term "sample preparation" and "pretreatment steps" used interchangeably herein refers to any steps or methods that treat a sample for downstream analysis of a target nucleic acid. Sample preparation may comprise various procedures needed to process the raw sample so that it is amenable to further analytical method, e.g., LC-MS method. It is important to note that at least one single sample preparation step should be compatible with downstream detection method in order to obtain optimal results.

Nucleic acids can be purified before or after quenching step during sample preparation, if necessary to remove substances which could be harmful (e.g., toxins), dangerous (e.g., infectious) or might interfere with the downstream analysis or the sensitivity of that analysis (e.g., metals, salts, protein, lipids). Purification may involve techniques such as chemical extraction with salts, chloroform or phenol, sedimentation centrifugation, chromatography or other techniques known to those of ordinary skill in the art.

As used herein, the term "target nucleic acid" refers to a nucleic acid comprising a "target sequence" to be analyzed, e.g., detected. Target nucleic acids may be DNA or RNA and may be either single-stranded or double-stranded. The target nucleic acid may include other sequences besides the target sequence that may not be analyzed. Typical target nucleic acids include virus genomes, bacterial genomes, fungal genomes, plant genomes, animal genomes, rRNA, tRNA, or mRNA from viruses, bacteria or eukaryotic cells, mitochondrial DNA, or chromosomal DNA.

In certain embodiments, the size of the target nucleic acid may 5, 15, 50, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725,750, 775, 800, 825, 850, 875,900, 925, 950, 975, 1000, 1100, 1200, 1300, 1400, 1500, 1750, 2000, 2250, 2500, 3000, 3500, 4000, 4500, 5000, 5500, 6000, 6500, 7000, 7500, 8000, 8500, 9000, 9500, 10000, 10500, 11000, 12000, 13000, 14000, 15000, 16000, 17000, 18000, 19000, 20000, 30000, 40000, 50000, 60000, 70000, 80000, 90000, 100000 or greater contiguous nucleotides, and any range derivable therein.

As used herein, the term "disulfide bond reducing agent" refers to an agent that reduces disulfide bonds, e.g., in proteins, in nucleic acids. Non-limiting examples include, dithiothreitol (DTT), ethylenediaminetetraacetic acid (EDTA), 2-mercaptoethanol, 2-mercaptoethylamine-HCl, (Tris(2-Carboxyethyl)phosphine)(TCEP), N-ethylmaleimide, cystein, or glutathione.

As used herein, the term "metal chelation agent" can include, e.g., a chemical entity capable of tightly binding or caging free metallic ions, sometimes with increased specificity. Non-limiting examples include EDTA, EGTA, BAPTA, Citrate, NTP, and dNTP.

As used herein, the term "detergent" can include, e.g., an ionic or non-ionic surfactant. Non-limiting examples include SDS, deoxycholate, and N-laurylsarcosine, NP 40, Tween 20, and Triton X-100.

As used herein, the term "salt" can be, e.g., a monovalent or multivalent salt. Non-limiting examples include (NH)SO, NaCl, KCl, and Na Citrate.

As used herein, the term "chaotrope" can include, e.g., a chemical that can disrupt the structure of water and/or promote the solubility of nonpolar substances in polar solvents such as water. Such behavior by chaotropes often results in the unfolding and inactivation of proteins or nucleic acids. Non-limiting examples include SCN–, Li+, CIO-4, and guanidinium.

As used herein, the term "missed cleavage" refers to a phosphodiester bond that is a predicted cleavage site that goes uncut.

As used herein, the term "single-mode chromatography" refers to chromatographic methods that is based on a single physical property, such as charge (ion-exchange chromatography, IEX), hydrophobicity (hydrophobic interaction chromatography, HIC), size (size exclusion chromatography, SEC), specific interactions (affinity chromatography, AC), or metal-chelating groups (immobilized metal ion affinity chromatography, IMAC).

As used herein, the term "multiple mode of chromatography" or "multimodal chromatography" refers to chromatographic methods that utilize more than one form of interaction between the stationary phase and analytes in order to achieve their separation. For instance, ion and hydrophobic interactions can occur at the same time, which frequently may increase the selectivity and specificity.

Nucleases

Nucleases are capable of degrading ribonucleic acid (RNA) and/or deoxyribonucleic acid (DNA). The nucleases may specifically degrade RNA or DNA, or may be nonspecific nucleases, such as Si nuclease and micrococcal nuclease, and degrade both RNA and DNA. The nucleases encompassed by the present disclosure include exonucleases and endonucleases.

Ribonucleases (RNases)

Non-limiting examples of ribonucleases that are inhibited using the present disclosure include, but are not limited to, RNase A, RNase B, RNase C, RNase 1, RNase T1, micrococcal nuclease, S1 nuclease, or DNase 1. Additional eukaryotic ribonucleases may be inactivated. Such as a member of a mammalian ribonuclease A Super family (i.e., ribonucleases 1-8), a member of an RNase H family, RNase L., eosinophil RNase, messenger RNA ribonucleases (5'-3' Exoribonucleases, 3'-5' Exoribonucleases), decapping enzymes and deadenylases. Additional ribonucleases that may be inhibited and/or inactivated by the methods of the present invention include E. coli endoribonucleases (RNase P, RNase III, RNase E, RNase I, RNase HI, RNase HII, RNase M, RNase R, RNase IV, F: RNase P2, O, PIV, PC, RNase N), E. coli exoribonucleases (RNase II, PNPase, RNase D, RNase BN, RNase T, RNase PH, OligoRNase, RNase R), RNase Sa, RNase F1, RNase U2, RNase Ms, and RNase St.

In some embodiments, RNA endonucleases are selected from the group consisting of RNase T1, RNase H, Cusativin, MazF, or Colicin E.

Both endonucleases and exonucleases can be inhibited by the methods of the present disclosure. One of skill in the art can readily employ the methods and compositions of the present disclosure to inhibit and/or inactivate other RNases known in the art beyond those specifically named herein.

Deoxyribonucleases (DNases)

Non-limiting examples of deoxyribonucleases that can be and/or inactivated using the present disclosure include, but are not limited to, DNase 1, S1 nuclease, and micrococcal nuclease. The methods of the present disclosure can be used to inhibit both endonucleases and exonucleases. One of skill in the art can readily employ the methods of the present technology disclosed herein to inhibit and/or inactivate other DNases known in the art beyond those specifically named herein.

The compounds e.g. chemical molecules used by the methods of the present technology in order to pretreat target nucleic acids can be in a liquid form or solid form such as a matrix comprising immobilized nuclease inhibitor. If liquid form is used, the composition may be, for example, a reagent used in molecular biology. Representative reagents that may be employed in the present invention include, but are not limited to, water, tris-ethylenediamine tetraacetic acid buffer (TE buffer), sodium chloride/sodium citrate buffer (SSC), 3-(N-morpholinol) propanesulfonic acid (MOPS), Tris buffer, ethylenediamine tetraacetic acid (EDTA), nucleic acid hybridization buffer, sodium acetate buffer, DNase or RNase digestion buffer, and nucleic acid storage buffer solution. One of skill in the art will understand that the methods of the present invention can be employed with compounds in addition to those named above.

Nuclease used in the present disclosure can cause digestion of a target nuclease, thereby creates a set of nucleic acid fragments containing a sequence which may be either homologous or complementary to the target sequence. Target sequences are fragmented, if necessary, into a plurality of fragments to create a set of fragments of uniform or non-uniform length. Sizes of nucleic acid fragments are between about 2 to about 1,000 nucleotides in length, preferably between about 10 to about 200 nucleotides in length, and more preferably between about 12 to about 100 nucleotides in length. Sizes in the range of about 2, 3, 4, 5, 10, 12, 15, 18, 20, 24, 26, 30 and 35 are useful to perform small scale analysis of short regions of a nucleic acid target. Fragment sizes in the range of 25, 50, 75, 125, 150, 175, 200, 250, 450, 650 nucleotides and larger are useful for rapidly analyzing larger target sequences.

In certain embodiments, the sizes of the nucleic acid fragments may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65,66, 67, 68, 69, 70, 71, 72, 73,74, 75, 76, 77, 78, 79, 80, 81, 82, 83, 84, 85, 86, 87, 88, 89,90,91, 92,93, 94, 95, 96, 97,98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725,750, 775, 800, 825, 850, 875,900, 925, 950, 975, 1000, 1100, 1200, 1300, 1400, 1500, 1750, 2000, 2250, 2500 or greater contiguous nucleotides, and any range derivable therein.

EXAMPLES

The following examples are included to demonstrate preferred embodiments of the technology. However, those of skill in the art should, in light of the present disclosure, appreciate that many changes can be made in the specific embodiments which are disclosed and still obtain a like or similar result without departing from the spirit and scope of the technology.

Example 1

RNase TI Digestion with a Compatible versus Incompatible Quench Step for IP-RPLC Luciferase mRNA, at a 1 mg/mL concentration in 10 mM Tris 0.1 mM EDTA pH 7.5 nuclease free buffer, was mixed as a 10 μL volume with 20 μL of 8 M Urea in 10 mM Tris 0.1 mM EDTA pH 7.5 nuclease free buffer. To this mixture, 10 μL of a dilute 100 U/μL RNase T1 (Worthington) was added and the reaction was allowed proceed for 5 min at 37° C. Replicate digest reactions were then quenched with three different conditions, either the addition of 40 μL dimethylsulfoxide (DMSO), 30 mg of guanidinium hydrochloride, or the extra addition of 30 mg urea. The final concentration of the samples ranges from approximately 0.15 to 0.20 mg/mL.

LC Conditions

A eluent: 1% hexafluoroisopropanol, 0.1% diisopropylethylamine in 18.2 MΩ water

B eluent: 0.075% hexafluoroisopropanol, 0.0375% diisopropylethylamine in 35:65 18.2 MΩ water/acetonitrile Samples: 0.2 mg/mL RNAse T1 digested mRNA LC System: Acquity H-Class Bio Binary Plus (Waters Technologies Corporation, Milford, MA)

Column: ACQUITY PREMIER BEH C18 300Å 1.7 µm 2.1×150 mm column (Waters Technologies Corporation, Milford, MA)

Flow: 0.4 mL/min

Gradient: 3-50% B in 60 min

Detection: UV at 260 nm

Column Temperature=70° C.

Injected volume: 5 µL

The results of Example 1 indicate that the 10 µg of the mRNA digested in a nuclease free Tris and EDTA pH 7.5 buffer must be quenched with special consideration given to compatibility of the sample composition with the downstream IP-RPLC analysis. When quenched with either DMSO or guanidinium hydrochloride, the LC injection led to breakthrough and there was no retention of the sample. See for example, FIG. 1A and FIG. 1B. Conversely, when extra amounts of urea were added for a quenching effect, sample components were well retained and resolved such that sequence mapping by LC-MS could be performed. (See, FIG. 1C).

Urea has been found to be desirable over DMSO and guanidinium hydrochloride because it facilitates loading onto the IP-RPLC separation. The present technology is not limited to the use of only urea (e.g., high concentrations of urea applied to quench the nuclease digestion); other non-ionic or potentially even anionic denaturants (like thiocyanate) could potentially be applied. Cationic denaturants are to be avoided as exemplified by the attempted use of guanidine. A cationic denaturant will compete for ion pairing interactions with the nucleic acid and be detrimental to IP-RPLC sample retention.

Example 2

RNase TI Digestion with a Urea and DTT Quench Step

Luciferase mRNA, at a 1 mg/mL concentration in 10 mM Tris 0.1 mM EDTA pH 7.5 nuclease free buffer, was mixed as a 10 µL volume with 20 µL of 8 M Urea in 10 mM Tris 0.1 mM EDTA pH 7.5 nuclease free buffer. To this mixture, 10 µL of a dilute 100 U/µL RNase T1 (available from Worthington) was added and the reaction was allowed proceed for 10 min at room temperature. The digest reaction was then quenched through the addition of 30 mg urea and a 5 µL volume of 1M dithiothreitol (DTT). The final concentration of the samples ranges from approximately 0.15 to 0.20 mg/mL.

LC Conditions

A eluent: 1% hexafluoroisopropanol, 0.1% diisopropylethylamine in 18.2 MΩ water

B eluent: 0.075% hexafluoroisopropanol, 0.0375% diisopropylethylamine in 35:65 18.2 MΩ water/acetonitrile Samples: 0.2 mg/mL RNAse TI digested mRNA LC System: Acquity H-Class Bio Binary Plus (Waters Technologies Corporation, Milford, MA)

Column: ACQUITY PREMIER BEH C18 300 Å 1.7 µm 2.1×150 mm column (Waters Technologies Corporation, Milford, MA)

Flow: 0.4 mL/min

Gradient: 3-50% B in 60 min

Detection: UV at 260 nm

Column Temperature=70° C.

Injected volume: 5 µL

Figure 2A:
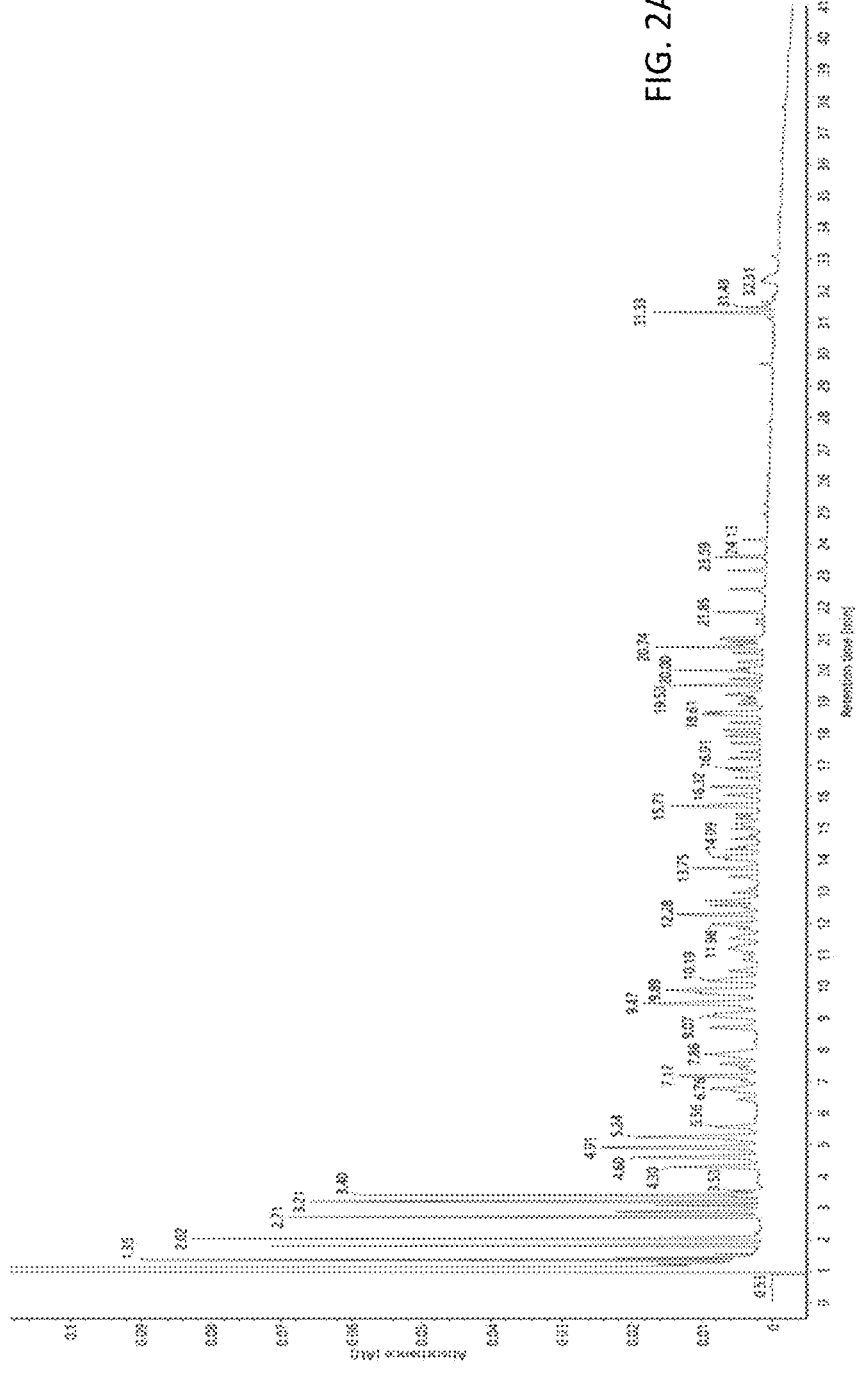
FIG. 2A and FIG. 2B display chromatograms for the separation of Luciferase mRNA obtained at two different time points. RNase T1 digest is quenched with urea and DTT.
Figure 2B:
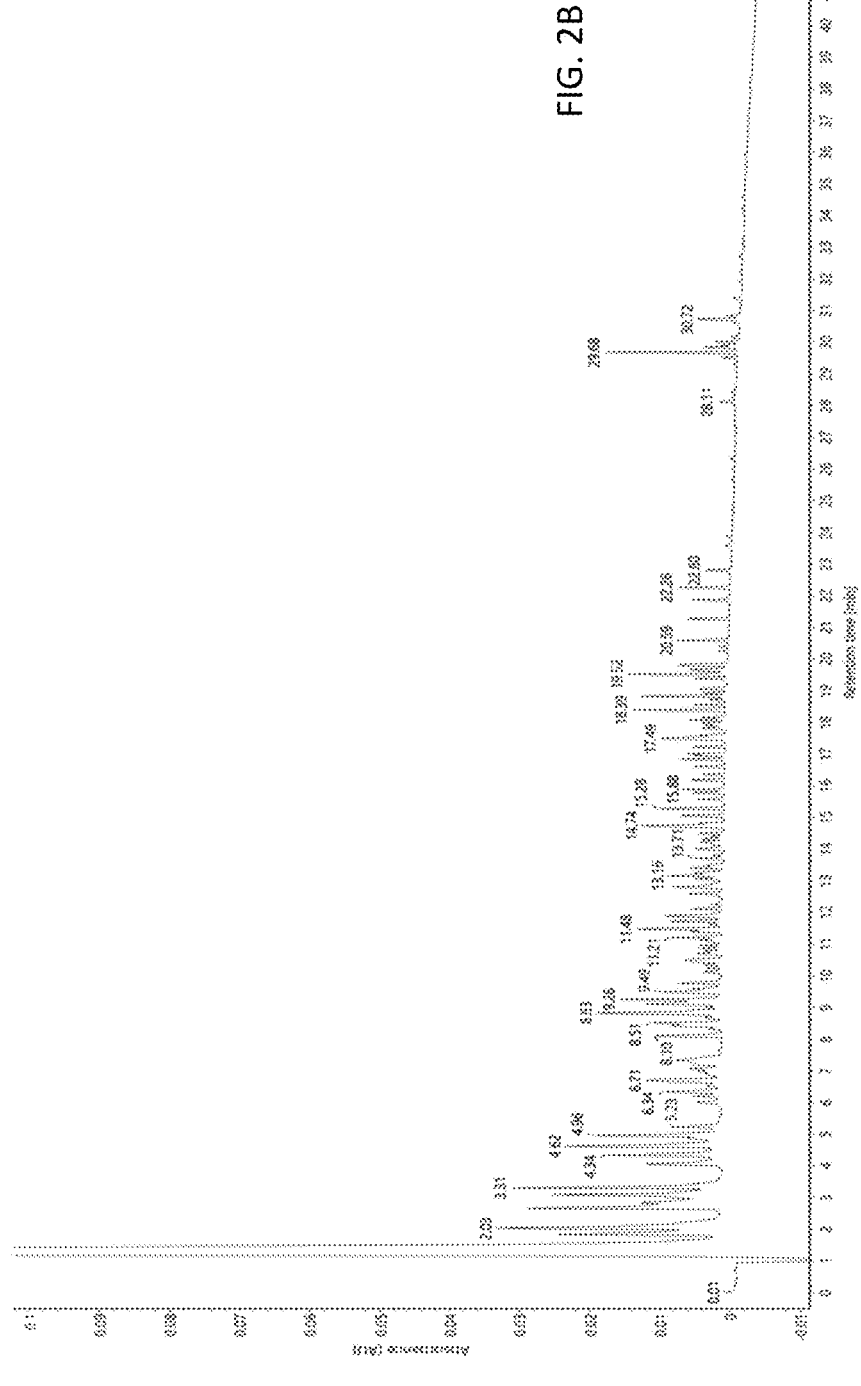

With this example, the RNAse T1 digestion was quenched with the extra addition of urea along with a small aliquot of concentrated reducing agent, namely dithiothreitol (DTT). This sample was analyzed on two different LC-MS instruments across a 3-day span and comparable fingerprinting was observed with each run, as shown in FIG. 2A and FIG. 2B. The results show how the methods presented in this disclosure can allow preserving the state of the sample for long lengths time that would facilitate repeat analyses and sample archiving.

While this disclosure has been particularly shown and described with reference to example embodiments thereof, it will be understood by those skilled in the art that various changes in form and details may be made therein without departing from the scope of the technology encompassed by the appended claims. For example, other chromatography systems or detection systems can be used.

What is claimed is:

1. A method for sequence analysis of a target nucleic acid present in a sample comprising the steps of:
  a. treating the sample with a nuclease free buffer comprising a first optional non-ionic or anionic denaturant and an optional metal-chelation agent to denature the target nucleic acid;
  b. incubating the sample with a nuclease enzyme for a predetermined amount of time, wherein the nuclease enzyme is capable of fragmenting the target nucleic acid to produce a set of nucleic acid fragments each containing a sequence that corresponds to a sequence of the target nucleic acid;
  c. inactivating the fragmenting capability of the nuclease enzyme by addition of a second non-ionic or anionic denaturant and an optional disulfide bond reducing agent;
  d. subjecting the set of nucleic acid fragments to a single-mode or a multiple mode of chromatography followed by a mass spectrometry (MS) method; and
  e. generating mass signals of the set of nucleic acid fragments by the mass spectrometry method whereby determining the sequence of the target nucleic acid from the mass signals.

2. The method of claim 1, wherein the target nucleic acid is selected from the group consisting of a single stranded DNA, a double stranded DNA, cDNA, a single stranded RNA, a double stranded RNA, a DNA/RNA hybrid, and a DNA/RNA mosaic nucleic acid.

3. The method of claim 1, wherein the optional disulfide bond reducing agent is selected from the group consisting of dithiothreitol (DTT), ethylenediaminetetraacetic acid (EDTA), 2-mercaptoethanol, 2-mercaptoethylamine-HCI, (Tris(2-Carboxyethyl)phosphine) (TCEP), N-ethylmaleimide, cysteine, or glutathione.

4. The method of claim 1, wherein the nuclease enzyme is selected from the group consisting of endonucleases and exonucleases.

5. The method of claim 4, wherein the endonucleases are selected from the group consisting of restriction enzymes, RNA endonucleases, DNA endonucleases and non-specific phosphodiesterases.

6. The method of claim 5, wherein the RNA endonucleases are selective or non-selective RNA endonucleases and the target nucleic acids is a single stranded RNA or a double stranded RNA.

7. The method of claim 6, wherein the RNA endonucleases are selected from the group consisting of RNase T1, RNase H, Cusativin, MazF, or Colicin E.

8. The method of claim 1, wherein the first optional non-ionic or anionic denaturant and the second non-ionic or anionic denaturant is independently selected from the group consisting of ureas, thioureas, sulfonylureas, semicarbazides, hydrazides, thiosemicarbazides, chaotropes, or salts thereof.

9. The method of claim 8, wherein the first optional non-ionic or anionic denaturant and the second non-ionic or anionic denaturant is independently selected from a group consisting of sodium thiocyanate, potassium thiocyanate, sodium dodecyl sulfate (SDS), urea, sodium iodide, sodium perchlorate, urea, a detergent, or salts thereof.

10. The method of claim 9, wherein the first optional non-ionic or anionic denaturant and second the non-ionic or anionic denaturant comprises urea, or a salt thereof.

11. The method of claim 1, wherein the length of the target nucleic acid is about 5 to about 100000 individual nucleotides.

12. The method of claim 1, wherein the single-mode or the multiple mode of chromatography comprises a reverse phase separation, a cation exchange separation, an anion exchange separation, an ion pair separation, normal phase separation, an ion mobility separation, a size-exclusion separation, a chiral separation, an affinity separation, a ligand exchange separation, a polar nonionic separation, or any combination thereof.

13. The method of claim 12, wherein the single-mode or the multiple mode of chromatography is coupled with an UV detection system.

14. The method of claim 1, wherein concentration of the second denaturant is between about 2M and about 8M.

* * * * *